US008081313B2

(12) United States Patent
Lam et al.

(10) Patent No.: US 8,081,313 B2
(45) Date of Patent: Dec. 20, 2011

(54) METHOD AND APPARATUS FOR MONITORING GAS CONCENTRATION IN A FLUID

(75) Inventors: Joseph K-W Lam, Bristol (GB); Norman Mark Ratcliffe, Bristol (GB); Stephen Smith, Bristol (GB)

(73) Assignee: Airbus Operations Limited, Bristol (GB)

( * ) Notice: Subject to any disclaimer, the term of this patent is extended or adjusted under 35 U.S.C. 154(b) by 197 days.

(21) Appl. No.: 12/114,864

(22) Filed: May 5, 2008

(65) Prior Publication Data

US 2009/0141280 A1 Jun. 4, 2009

(30) Foreign Application Priority Data

May 24, 2007 (GB) .................................. 0709935.1
Jul. 24, 2007 (GB) .................................. 0714376.1

(51) Int. Cl.
  *G01N 21/00* (2006.01)
(52) U.S. Cl. ........................................................ 356/436
(58) Field of Classification Search ........................ None
  See application file for complete search history.

(56) References Cited

U.S. PATENT DOCUMENTS

| 4,764,343 A | 8/1988 | Nyberg |
| 5,030,420 A | 7/1991 | Bacon et al. |
| 5,043,285 A | 8/1991 | Surgi |
| 5,919,710 A | 7/1999 | Gord et al. |
| 6,251,342 B1 | 6/2001 | Narula et al. |
| 6,531,097 B1 | 3/2003 | Vojnovic et al. |
| 7,356,464 B2 * | 4/2008 | Stella et al. ..................... 704/210 |
| 7,456,969 B2 * | 11/2008 | Chabanis et al. .............. 356/437 |
| 2004/0062683 A1 | 4/2004 | Yam et al. |
| 2006/0060788 A1 * | 3/2006 | Uchida et al. .................. 250/343 |
| 2006/0171845 A1 | 8/2006 | Martin et al. |
| 2007/0070356 A1 | 3/2007 | Tan et al. |
| 2007/0122311 A1 | 5/2007 | Shahriari |

FOREIGN PATENT DOCUMENTS

| GB | 2132348 | 7/1984 |
| WO | W09212424 A1 | 7/1992 |
| WO | 00/42418 | 7/2000 |
| WO | 03046422 A1 | 6/2003 |
| WO | 2004044547 A3 | 5/2004 |

OTHER PUBLICATIONS

UK Search Report for GB0714376.1 dated Nov. 26, 2007.
UK Search Report for GB0813715.0 dated Nov. 5, 2008.
Xavier et al. Oxygen Sensing in Nonaqueous Media Using Porous Glass with Covalently Bound Luminescent Ru(II) Complexes Analytical Chemistry, vol. 70, No. 24, pp. 5184-5189, Dec. 15, 1998.

* cited by examiner

*Primary Examiner* — Tu Nguyen
(74) *Attorney, Agent, or Firm* — Lowe, Hauptman, Ham & Berner, LLP

(57) ABSTRACT

A monitor for monitoring gas concentration in an aerospace application is described, one such application being measuring the concentration of oxygen in or next to aviation fuel. The monitor comprises: a substance, the spectroscopic properties of which change when the substance is exposed to the gas; a light source, arranged to irradiate the substance with light; and a photosensor, arranged to detect light from the substance. The substance may be mounted on a solid substrate.

33 Claims, 5 Drawing Sheets

METHOD AND APPARATUS FOR MONITORING GAS CONCENTRATION IN A FLUID

RELATED APPLICATIONS

The present application is based on, and claims priority from, British Application Number 0714376.1 filed Jul. 24, 2007 and British Application Number 0709935.1 filed May 24, 2007, the disclosures of which are hereby incorporated by reference herein in their entirety.

FIELD OF THE INVENTION

This invention relates to monitoring gas concentration in a fluid. More particularly, although not exclusively, the present invention may find specific application in the aerospace industry, for example in commercial passenger aircraft. Even more particularly, although not exclusively, the present invention relates to measuring the concentration of oxygen that is dissolved in aviation fuel or that exists in an ullage over the fuel.

BACKGROUND ART

Aircraft fuel naturally contains some dissolved gas, typically air, and therefore fuel typically contains some dissolved oxygen. The amount of oxygen in fuel decreases with pressure. Therefore, at cruising altitude (i.e., at low ambient pressure), oxygen is degassed from the fuel. From a safety standpoint, it is desirable to have fuel or fuel-rich environments contained or embedded in an inert atmosphere. Thus, the release of oxygen from fuel in such an environment is highly undesirable.

Also, evolved gas from the fuel may increase the risk of air pockets forming in the fuel system of the aircraft. Some aircraft fuel-tank arrangements use gravity feed systems including siphons, to transfer fuel within the fuel system. Air pockets present in the fuel tank system may act to disrupt the siphon effect in gravity feed systems, the pressure head possibly being insufficient to push the air down the pipes. Consequently air pockets could be created, which can interfere with fuel flow in the pipes.

A known technology for estimating oxygen concentration in gas and liquid uses electrochemical detection. A prior-art sensor comprises an electrochemical cell with an anode and a cathode in an electrolyte solution. The electrochemical cell is separated by a membrane from a (gas or liquid) sample, the oxygen concentration of which is to be measured. Oxygen diffuses from the sample across the membrane into the electrochemical cell to establish fugacity equilibrium. The fugacity is proportional to the ambient oxygen concentration. A change in oxygen concentration in the electrolyte causes a change in its electrical property and a resulting change in electric current through the system. The current is proportional to the oxygen concentration in the electrolyte. The operating limits and sensitivity of the sensor are characterised by the electrolytes used. However, most commonly used electrolytes are not suitable for extreme operating temperatures. In particular, they are not suitable for the low temperatures encountered in aviation applications.

W A Rubey et al. (Journal of Chromatographic Science, Vol. 33, 1995, 433-437) describe a method for the analysis of atmospheric gases and other small molecules in thermally stressed jet fuel. As with the method employed by V V Malyshev et al. (Trudy, KIIGA, 1970, p 3), the chromatographic method uses packed columns for separation of permanent gases. Although the analytical system of Ruby et al. allows monitoring of fuels in a continuous, flowing, high-pressure stream, the system is overly complex, containing many switching valves and three co-joined columns. It is thus completely impractical for in situ aerospace applications.

A method for the analysis of dissolved gases in insulating oil by gas chromatography is described in ASTM International Designation D3612-02 "Standard Test Method for Analysis of Gases Dissolved in Electrical Insulating Oil by Gas Chromatography" (available from ASTM International, 100 Barr Harbor Drive, PO Box C700, West Conshohocken, Pa., 19428-2959 USA). However, this method would not be readily applicable to the aviation fuel, as it would not allow for "in-line monitoring" given the complexity of gas chromatography equipment.

Thus, the above prior art does not provide a method or apparatus that enables fast and accurate monitoring of the concentration of oxygen in aircraft fuel or in the fuel tank ullage of an aircraft or aircraft vehicle.

A further proposal of the prior art, disclosed in U.S. Pat. No. 5,919,710 (Gord et al), relates to the measurement of dissolved oxygen in fuel flowing in a fuel line by means of doping the fuel with a luminophore and measuring the phosphorescence of the luminophore when excited by a pulse of laser light (i.e. a coherent light source). The oxygen concentration is related to the decay in light intensity phosphoresced by the luminophore (the luminescence lifetime). The method requires the bulk doping of fuel with a luminophore. Such a method can not therefore be viewed as a viable and practical method of measuring oxygen concentrations in fuel in commercial aerospace applications, as the bulk doping of fuels with such luminophores would be impractical. Such a method also has application only in relation to measuring dissolved gas concentrations in liquids.

The need to provide a coherent light source in accordance with the teachings of Gord et al would appear to envisage the provision of relatively high power laser devices. For example, the pulsed laser light provided in accordance with the teachings of Gord et al would appear to have a peak power density (the peak optical power per cross-sectional area of laser beam) of greater than 10 megawatts per $cm^2$. Such relatively high peak power densities would appear possible (i.e. without significant safety risks) in Gord et al by virtue of the fuel flowing when exposed to the laser light. Whilst such high peak power densities may not cause significant ignition risks in relation to moving fuel, using relatively high powered pulsed laser light in a static fuel environment could give rise to significant safety risks. It would seem that the proposal of Gord et al would not therefore be of practical application either in relation to the measurement of oxygen concentrations in a fuel tank or in relation to the measurement of oxygen concentrations in or next to fuel in commercial passenger aircraft, because of safety and/or aviation certification issues.

The present invention seeks to ameliorate at least some of the above-mentioned problems. Alternatively, or additionally, the present invention seeks to provide an improved apparatus and method for detecting gas levels in aerospace applications. Alternatively, or additionally, the present invention seeks to provide an improved apparatus and method for safely detecting gas levels in aerospace applications, where fuel is present.

DISCLOSURE OF THE INVENTION

In a first aspect, the invention provides a monitor for monitoring gas concentration in a fluid comprising aviation fuel, the monitor comprising:

a) a substance, the optical properties of which change when the substance is exposed to the gas;
b) a light source, arranged to irradiate the substance with light; and
c) a photosensor, arranged to detect light from the substance.

In a second aspect, the invention provides a method of monitoring a gas concentration in a fluid comprising aviation fuel, the method comprising:
a) providing in a vessel containing the fuel a substance, the optical properties of which substance change when the substance is exposed to the gas;
b) exposing the substance to light;
c) detecting light from the substance; and
d) monitoring for changes in the detected light to indicate changes in the concentration of the gas in the region of the substance.

Embodiments of the present invention can advantageously be used in inerting applications in aviation to provide a fast and accurate means of monitoring the oxygen concentration level in the fuel or the ullage. With knowledge of the oxygen concentration level, a smart inerting system may control the injection of Nitrogen Enriched Air (NEA) to dilute the oxygen concentration above the fuel and thus reduce or eliminate the risk of fuel or fuel-vapour ignition in the fuel system of the aircraft.

Embodiments of the invention can advantageously be used in fuel-flow control applications in aviation to provide a fast and accurate means of monitoring the dissolved oxygen concentration in fuel. With knowledge of dissolved oxygen concentration in fuel, the risk of air pockets in pipes under gravity feed conditions may be gauged and appropriate action taken.

Certain embodiments of the present invention adapted for measuring the concentration of a gas in or next to an aviation fuel provide the benefit of using optical technology in a fuel-rich environment. In contrast, alternative technologies may require the use of electrical power and conduction paths. This may introduce extra risk of fuel or fuel-vapour ignition in the fuel system. The monitor of the present invention may, in certain embodiments, be capable of operation without any electrical current passing through or in a region where fuel or fuel vapour is present.

The fluid comprising the fuel may be a liquid, may be a gas or may comprise both a liquid phase and a gaseous phase. The monitor may be adapted so as to be suitable for measuring gas concentration in a liquid comprising fuel. Alternatively, or possibly additionally, the monitor may be adopted so as to be suitable for measuring gas concentration in a gaseous environment. The fluid may for example consist of fuel vapour. The concentration of the gas in liquid aviation fuel may be monitored directly, with the substance immersed in the fuel. The concentration of the gas in liquid aviation fuel may be monitored indirectly, with the fuel being contained in a container having an ullage above the fuel and the substance being positioned in the ullage. (The concentration of the gas in the ullage will of course be related to the concentration of the gas in the fuel, assuming equilibrium has been reached).

The gas may be dissolved in the fuel.

The term "light" as used herein refers to electromagnetic waves that are infrared, visible or ultraviolet, and the term "optical properties" is to be understood accordingly.

The photochromic sensor is preferably able to operate at extreme operating-temperatures, where the current technology of electrochemical sensors fails.

The aviation fuel may be a petroleum fuel. The petroleum fuel may be a jet fuel. The petroleum fuel may comprise kerosene. The petroleum fuel may comprise a naphtha-kerosene. The petroleum fuel may be Jet A, Jet A-1 or Jet B, or TS-1, for example.

The gas may be oxygen. The gas may be nitrogen. The gas may be carbon dioxide. The gas may be argon. The gas may be helium. The gas may be neon. The gas may be hydrogen.

The substance may be a photochromic substance. The substance may be an organic dye or pigment. The substance may comprise a chromophore or a chromophore moiety. The substance may comprise a chromophore-metal complex. The substance may be an organo-metallic complex, the absorption or emission spectrum of which changes with binding of the gas to the complex. The change may be a change in the absorption of the light from the light source. The substance may exhibit photoluminescence (for example fluorescence or phosphorescence) induced by the light from the light source, and the change may be a change in the photoluminescence. The change may be a reduction in the photoluminescence of the substance when irradiated with light. The change may be an increase in the photoluminescence of the substance when irradiated with light. The change may be a change in the phosphorescent properties of the substance when irradiated with light, for example a change in the intensity of radiation initially emitted by the substance or a change in the decay of radiation observed after cessation of the irradiation of the substance.

The substance may be a porphyrin. The porphyrin may include a metal ion. The porphyrin may include a platinum ion.

The substance may be carried by a substrate. The substrate may for example be coated with the substance. The substance may be embedded in the substrate. The substrate is preferably solid. The substance may be carried by the substrate in such a way as to eliminate (or at least substantially eliminate) leaching of the substance into the fluid during use. The substance may for example be bonded to the substrate. Leaching of the substance into the fluid may be reduced or eliminated by means of a gas permeable barrier.

The monitor may be used to measure the concentration of a gas in a fluid in a vessel. The monitor may be mounted inside the vessel. The vessel may be a conduit for transporting the fluid. The vessel may be a container. The container may be or may be part of a vehicle carrying the fuel. The container may be a fuel tank of an aircraft. The vessel may be a fuel pipe. The monitor may be so configured and arranged as to be suitable for mounting in a fuel tank. For example, the monitor may be so arranged that it is not necessary to have high electrical power, voltage or current or high intensity light sources in the fuel tank. The monitor may be so configured and arranged as to be suitable for use in a passenger aircraft.

The light source may be a light-emitting diode (LED). The light source may comprise one or more LEDs. The or each LED may be low-power LEDs. For example, the LEDs may be configured to be operated by means of electrical power of less than 500 mW and preferably less than 100 mW. The or each LED may for example be arranged to emit light having a maximum radiant intensity of less than 10 W/Sr (Watts per Steradian) and possibly less than 1 W/Sr. The or each LED may be arranged to emit light having a maximum power density of less than 1 kilowatt per $cm^2$ and possibly less than 10 watts per $cm^2$. The light source when provided in the form of one or more LEDs may have the advantage of having a relatively long life span. For example, the estimated time to failure for the or each LED may exceed 10,000 hours of use. The average life time of the or each LED may therefore exceed several years, thereby requiring little or no maintenance. The light source may be a laser. The light to which the substrate is exposed may be ultraviolet (UV) light. The light source may be an electric light source. The light source may comprise a filament light bulb. The light source may comprise a fluorescent tube. The light source may comprise one or more filters. The light source may be pulsed during operation of the monitor, such that the light source irradiates the substance with pulsed light. Preferably, however, the light source is arranged to irradiate the substance with light of a substantially constant intensity during operation of the monitor.

The photosensor may comprise a photodiode. The photosensor may detect light in the visible spectrum. The monitor may comprise a filter arranged between the photosensor and the substance. The filter may absorb substantially all light from the light source that is incident upon the filter. The filter may transmit light from the substance.

The monitor may be arranged to output a signal dependent on the intensity of light detected by the photosensor. The monitor may be arranged to output a signal, which varies in inverse proportionality to changes in the electrical signal outputted directly by the photosensor. The monitor may be arranged to output a signal, which is dependent on, for example proportional to, the concentration of the gas in the fluid as measured by the monitor. The output of the monitor may be derived from a measurement of the intensity of light as detected by the photosensor at a time when the substance is being irradiated by the light source. Alternatively, or additionally, the output of the monitor may be derived, at least in part, from a measurement of the intensity of light as detected by the photosensor at a time when the substance is not being irradiated by the light source. Any of the outputted signals mentioned herein may be outputted by the monitor, by a unit associated with and forming part of the monitor or by a unit associated with, but separate from, the monitor.

It is of course preferable for the monitor to be able to operate at the typical operational temperatures of an aircraft. The concentration of gas may be measured at temperatures of less than −15° C. and possibly less than −25° C. For example, the concentration of gas may be measured at temperatures as low as temperatures of the order of −40° C., and possibly lower. The monitor may be able to operate at all temperatures at which the fuel exists in a liquid phase at atmospheric pressure.

In a third aspect, the invention provides a vessel, for example a container or a conduit, including a sensor according to the first aspect of the invention. The present invention has particular, but not exclusive, application when the vessel is in the form of an aircraft fuel tank in a commercial passenger aircraft.

In a fourth aspect, the invention provides a vehicle, for example an aircraft or a fuel tanker, including a vessel according to the third aspect of the invention. The present invention has particular, but not exclusive, application when the vehicle is in the form of a commercial passenger aircraft. The aircraft may for example be heavier than 50 tonnes dry weight, and may be heavier than 200 tonnes dry weight. The aircraft may be of a size equivalent to an aircraft designed to carry more than 75 passengers, and possibly more than 200 passengers.

In a fifth aspect, the invention provides a method of controlling the environment in which an aviation fuel is stored, the method including a step of measuring the concentration of a gas in the environment by means of either the first or second aspects of the present invention. Thus, the method may include a step of measuring the concentration of the gas in the environment using a monitor according to the first aspect of the invention. The method may include a step of measuring the concentration of the gas in the environment by means of performing the method according to the second aspect of the invention. The concentration of gas measured may be the concentration of gas in the fuel and/or the concentration of gas in the ullage space above the fuel. It will be understood that the environment in which the fuel is stored may be in the form of a vessel, for example a container comprising the fuel and ullage space above the fuel.

The measuring of the concentration of the gas in the environment may be performed periodically. For example, the gas concentration may be monitored by means of performing several measurements every second.

The method may further comprise a step of taking action in dependence on the gas concentration so measured. There may for example be a step of introducing a different gas into the environment comprising the fluid, for example so as to dilute the concentration of gas so measured. The method may include a step of inerting the environment in which the fuel is stored. For example, if the gas concentration meets a certain criterion (for example, if the oxygen concentration exceeds a predetermined threshold) the ullage space may be inerted by means of introducing an inerting gas. The method may comprise a step of degassing the fuel. For example, if the monitoring of the concentration of gas in the fuel indicates that too much gas is dissolved in the fuel it may be desirable to release some of the gas from the fuel by means of degassing the fuel, for example, by agitation of the fuel by suitable means. Degassing of the fuel may for example have the benefit of reducing the likelihood of super-saturation of gas in jet fuel that might otherwise occur. Super-saturation of jet fuel may give rise to the increased risk of large amounts of rapid gas release in an aircraft fuel system, potentially giving rise to flow problems in the fuel system and associated pipe-work. Above a step of action is taken in the case where the gas concentration so measured is deemed to be too high. Of course, there may be applications where it is desirable to take action if the gas concentration as measured is deemed to be too low. There may for example be step of introducing more gas of the same type as that being measured into the environment comprising the fluid, so as to increase the concentration of the gas.

In accordance with an embodiment of this fifth aspect of the invention there is provided a method of inerting an aviation fuel, the method including the step of monitoring the concentration of a gas in the fuel using a sensor according to the first aspect of the invention or performing a method according to the second aspect of the invention. There is also provided a method of degassing an aviation fuel, the method including the step of monitoring the concentration of a gas in the fuel using a sensor according to the first aspect of the invention or by means of performing the method according to the second aspect of the invention.

Other applications of the invention are envisaged in the aerospace industry. For example, a monitor similar to that of the first aspect of the invention may be used to monitor gas concentration in a fluid, which does not necessarily comprise aviation fuel. Such a monitor may for example comprise a) a substance, the optical properties of which change when the substance is exposed to the gas;
   b) a light source, arranged to irradiate the substance with light; and
   c) a photosensor, arranged to detect light from the substance.

The fluid may be air. The gas to be monitored may be oxygen. The gas to be monitored may be carbon monoxide. The gas to be monitored may be water vapour. A monitor embodying this modified version of the first aspect of the invention may for example be used to monitor gas, for example oxygen, levels in the aircraft cabin. A monitor embodying this modified version of the first aspect of the invention may for example be used to monitor gas, for example oxygen, levels in the hold of the aircraft. A monitor embodying this modified version of the first aspect of the invention may for example be used to monitor gas, for example oxygen, levels in an area of the aircraft for carrying people and/or animals. The monitor may form part of an airport vehicle, such as for example an aircraft, an airport coach, a fuel truck, an aircraft-towing vehicle, or the like.

Similarly, a method similar to that of the second aspect of the invention may be performed to monitor a gas concentration in a fluid, which does not necessarily comprise aviation fuel. Such a method may comprise the following steps:
 a) providing in a vessel containing the fuel a substance, the optical properties of which substance change when the substance is exposed to the gas;
 b) exposing the substance to light;
 c) detecting light from the substance; and
 d) monitoring for changes in the detected light to indicate changes in the concentration of the gas in the region of the substance.

It will be appreciated that these modified first and second aspects of the present invention may utilise features described herein with reference to other aspects of the invention. The invention is of particular application in the aerospace industry. For example the invention may be of application in or on an aircraft. Also, the above-descried method may be performed on an airport vehicle. The vessel mentioned above may be a container, such as a fuel tank. Alternatively, the vessel may be a conduit via which the fluid is arranged to flow.

It will be appreciated that aspects of the present invention described in relation to the method of the present invention are equally applicable to the apparatus of the present invention and vice versa.

BRIEF DESCRIPTION OF THE DRAWINGS

Certain illustrative embodiments of the invention will now be described in detail, by way of example only, with reference to the accompanying schematic drawings, in which.

DETAILED DESCRIPTION

Figure 1:
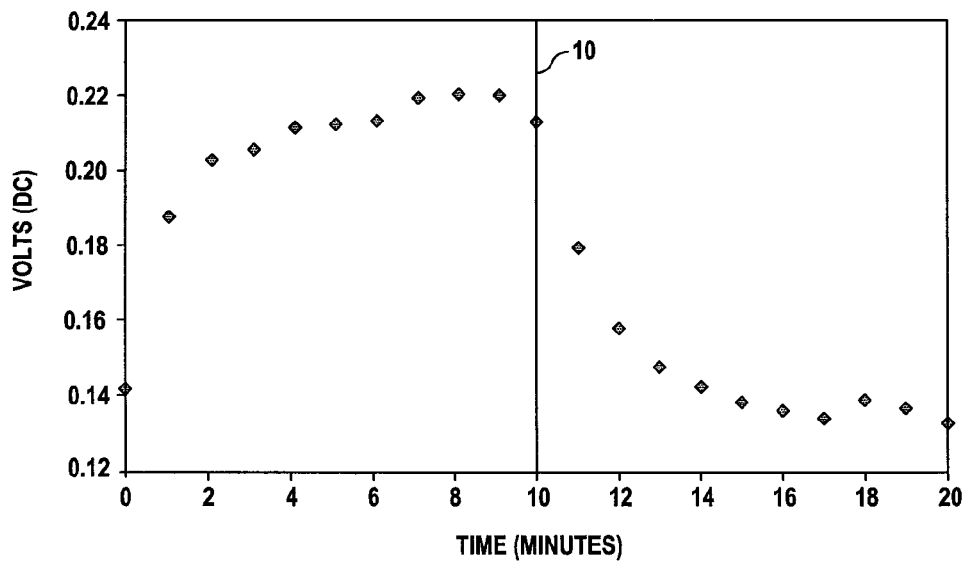
FIG. 1 is a plot of recorded photodiode voltage against time in an experiment in which kerosene is degassed under vacuum, the photodiode voltage arising from phosphorescence of a porphyrin dye under irradiation from a UV LED.

In order to improve the design of fuel-management systems it is desirable to understand how air degasses from jet fuel at operational altitudes, and to measure the concentration of gas in the liquid fuel or in the ullage over the fuel. It has been found that the use of photochromic detection techniques provides a viable method of monitoring of gas concentrations in real-life aerospace applications. In particular, such techniques enable reliable measurement of the gas content in a liquid or vapour over the wide range of temperatures that are encountered during operation of an aircraft or airport vehicle. For example, accurate measurements may be made as low as −40° C. Photochromic detection techniques have also been found to be sufficiently sensitive to detect low levels of gas concentration. To this end, oxygen concentrations at very low levels from 100 to 10 parts per million were readily detectable with the methodology according to embodiments of the invention. Experimental processes will be described below to illustrate various aspects of the invention. In particular, an illustrative example, namely, the novel determination of the degassing profile of kerosene in a controlled environment and at varying simulated altitudes and agitation rates will be described in detail as follows.

The method according to one aspect of the invention relies on light irradiation phosphorescence quenching of a dye with oxygen. A photochromic material was placed in gaseous and liquid samples, and irradiated with ultraviolet (UV) light from a UV-light-emitting diode (LED). In a dark environment, the material phosphoresced bright red in a de-oxygenated environment and dull pink in an oxygenated environment. The change in phosphorescence of the irradiated material was directly dependent on the oxygen concentration of the sample in which it was immersed.

To allow quantification of the visual observation, a micro photodiode light meter was used to measure the phosphorescence of the material. A change in the phosphorescence produced a change in the electrical voltage of the light-meter system. The voltage was calibrated according to the oxygen concentration. A colour filter was placed in front of the photodiode to decrease the risk of interference from ambient light and scattered UV light.

There are several chemical classes of compounds capable of exhibiting phosphorescence quenching, and it is expected that several of them will be suitable for use in sensors for oxygen in aviation fuel—being one application envisaged for the present invention. The selection of such compounds will be clear to the skilled person and will not be elaborated further.

The class of compound used in this exemplary embodiment is the class of porphyrins, a class that is considered to be superior in showing a phosphorescence phenomenon.

In the context of measuring oxygen concentration in kerosene (simulating jet fuel), it has been found that the oxygen content can be readily measured by monitoring the degree of phosphorescence of a platinum porphyrin, the metal complex Pt(II) meso-tetra(pentafluorophenyl) porphyrin (Porphyrin A).

Initial analyses were carried out using a porphyrin-A-based paint coating which was sprayed onto an aluminium backing. When the material was exposed to air, the oxygen present in the air prevented the material from phosphorescing. However, when a jet of nitrogen was flushed over the surface, thus sharply reducing the oxygen content of the environment, the material showed an intense red phosphorescence. This resulted in a very localised region of phosphorescence that was easily detectable by the naked eye.

A subsequent experiment utilised the above method for detecting gas concentrations in toluene. To this end, aluminium strips (6 mm×25 mm) coated with Porphyrin A were cut, and placed in a UV transmissive cuvette made of Poly (methyl methacrylate) (PMMA). The cuvette was then filled with sufficient toluene to cover the strips. A probe was inserted into the cuvette to allow nitrogen to be bubbled through thereby deoxygenating the toluene.

UV light (of wavelength 400 nm) from an LED was used to promote phosphorescence in the porphyrin coating. The UV LED and the nitrogen supply were switched on and any changes in phosphorescence recorded by means of a qualitative, visual comparison. Phosphorescence was observed after a short period of deoxygenating with nitrogen and was very clear to the naked eye.

The experiment was then repeated with the fuel substitute kerosene, instead of toluene. According to this variant, phosphorescence of the coated strip was readily observed at different amounts of oxygen, and the effect was reversible.

The porphyrin complex dissolved in the kerosene and the coated strip became less active within minutes. However in this variant, the kerosene solution itself started to phosphoresce due to the dissolved porphyrin. Preliminary trials with the dye dissolved in the kerosene showed that phosphorescence and quenching could be reversibly and readily demonstrated with aerating, degassing and illumination with a UV LED.

The above-mentioned process was quantitatively analysed by using a micro-photodiode light meter to measure the increase in phosphorescence on degassing the fuel. This is described in detail as follows.

10 ml of kerosene, with dye added, and a magnetic stirring flea were placed in a polytetrafluoroethylene (PTFE)-septum-topped vial. A needle connected to a vacuum line was inserted through the septum to allow the kerosene to be degassed in a controlled manner. Ambient light was excluded from the vial by covering the exterior in tin foil with a window left to allow positioning of two UV LEDs and the photodiode detector. The LEDs were placed midway up liquid level with the photodiode placed immediately above. A piece of Ilford colour filter (608 spectrum red) was placed in front of the photodiode to reduce interference from ambient light and UV light from the LEDs.

With the vacuum set at 7 mm Hg/720 mm Hg Gauge pressure the liquid was stirred. After 55 seconds of stirring, the fluid was allowed to settle and then a voltmeter reading from the photodiode was recorded. The stirring was then resumed. This process was repeated for a total of 10 minutes. After 10 minutes (line 10 in FIG. 1) the vacuum was released and the process repeated to record the subsequent dissolving of gases back into solution.

FIG. 1 shows the results for the kerosene phosphorescence experiment. There was a marked increase observed in the recorded voltage over the first 2 minutes, which was expected. Exposure to vacuum initially gave rapid degassing, and as the dissolved gases reduced in concentration so did the rate of degassing and subsequently the rate of change of the recorded phosphorescence.

The positioning of the LEDs with respect to the photodiode was also tested and two alternative arrangements were tried. The first was with the LEDs and photodiode placed midway up the liquid but on opposite sides of the vial and the second was with the photodiode at right angles to the LEDs.

The position of the photodiode relative to the LEDs was found to be important for optimizing for maximum sensitivity. The most sensitive arrangement of those tested was the configuration where the LEDs and photodiode were placed one above the other, and on the same side of the vial. When the photodiode and the LEDs were on opposite sides of the vial, the LEDs produced too much interference. When they were placed at right angles the sensitivity was greatly reduced.

Subsequent experiments focussed on the measurement of the oxygen concentration in kerosene at a range of pressures and agitation rates. The apparatus used is shown in FIG. 2.

A standard solution was prepared by dissolving 0.010 g Porphyrin A in 100 ml kerosene giving a concentration of 100 mg $l^{-1}$. This solution was then diluted further by adding 10 ml of the prepared standard to a volumetric flask and making up to 250 ml with kerosene to give a final test solution 120 concentration of 4 mg $l^{-1}$.

Figure 2:
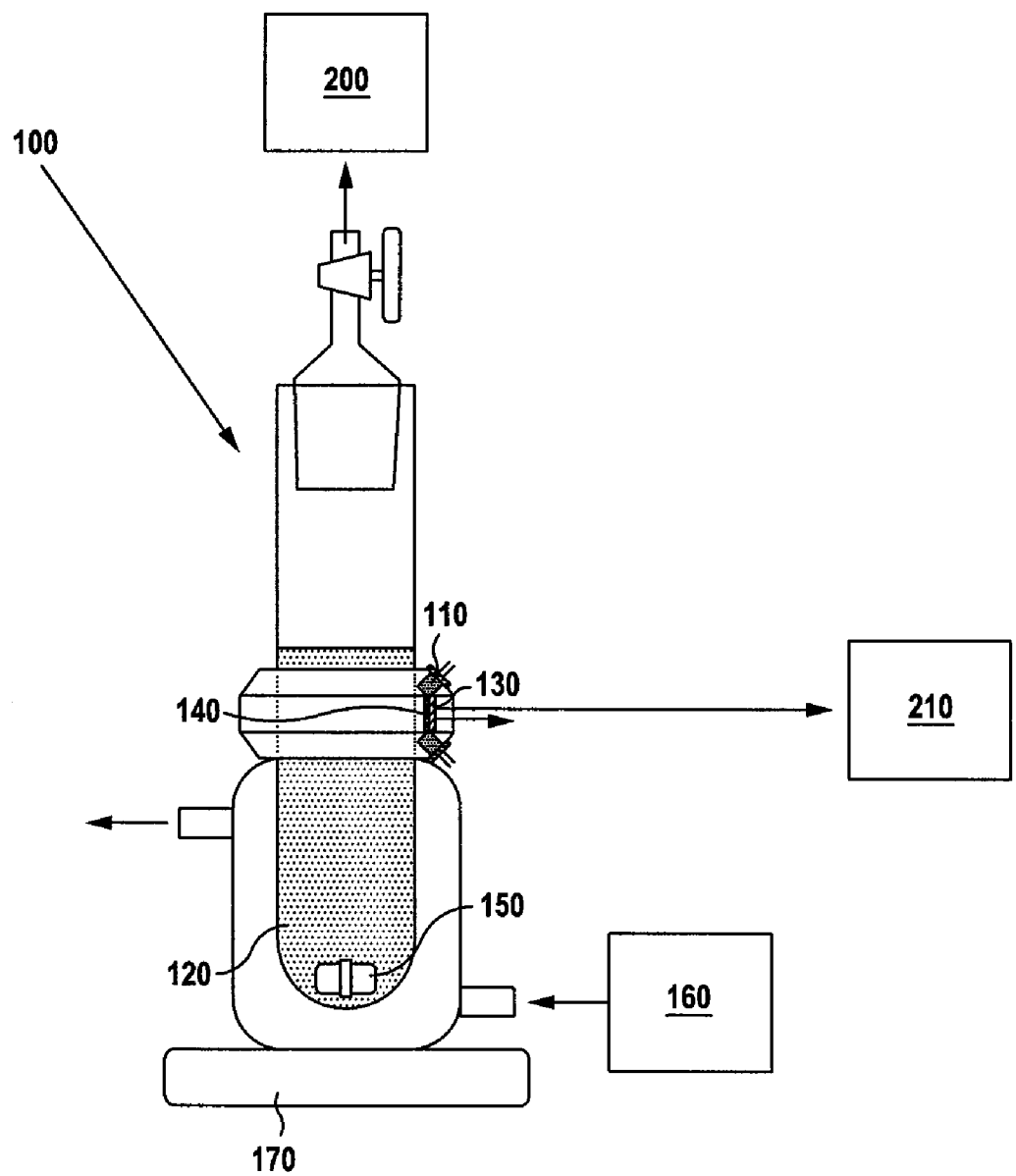
FIG. 2 is a side view of apparatus used to determine degassing of kerosene at a range of pressures and agitation rates.

The test chamber 100 was configured as shown in FIG. 2. Two 395 nm UV LEDs 110, UV-395-TO92, were situated at 45 degrees to the test chamber 100 and focused on a point approximately 5 mm into the solution 120. The photodiode 130 was positioned between the LEDs 110 in close proximity to the test vessel 100 so as to maximise the amount of phosphorescence detected. Direct illumination of the photodiode 130 by the UV LEDs 110 was minimised by the introduction of a red filter 140, Ilford colour filter No. 608, immediately in front of the photodiode 130. Ambient light was excluded by enclosing the apparatus and situating it in a blacked out fume hood.

Aliquots of 25.00 g (+0.01 g) of the Porphyrin-A/kerosene solutions were weighed out prior to each experiment. The aliquot and a magnetic follower 150 were added to the temperature-controlled test chamber 100 maintained at 20° C. using a temperature-controlled water bath 160. Different stirring rates were set for different experiments using an Ikamag digital stirring plate 170, and the solution allowed to equilibrate at ambient pressure and open to the atmosphere. Equilibration was considered complete when the photodiode output voltage remained constant, ±0.001 V, for a 10 minute period.

When a constant output voltage from the photodiode 130 had been reached, the ballast chamber 200 was reconnected and the data-logging software 210 was reset. Following a 30 second delay, the test chamber was exposed to a preset simulated altitude and maintained to within 1% of the desired value using a Fairchild 16212H vacuum regulator. Pressure data were recorded in real time using a suitable pressure transducer linked to the data logging software. Data collection for the change in photodiode 130 output and pressure were continued until a plateau was reached and remained steady for 10 minutes.

Samples at stirring rates of 500, 700, 900, 1000 and 1100 rpm were each exposed to pressures equivalent to altitudes from 5000 to 45000 feet in 5000 feet intervals and the photodiode 130 output voltage and pressure data recorded. A fresh aliquot of Porphyrin A/kerosene solution 120 was used for each agitation rate and simulated altitude.

Figure 3:
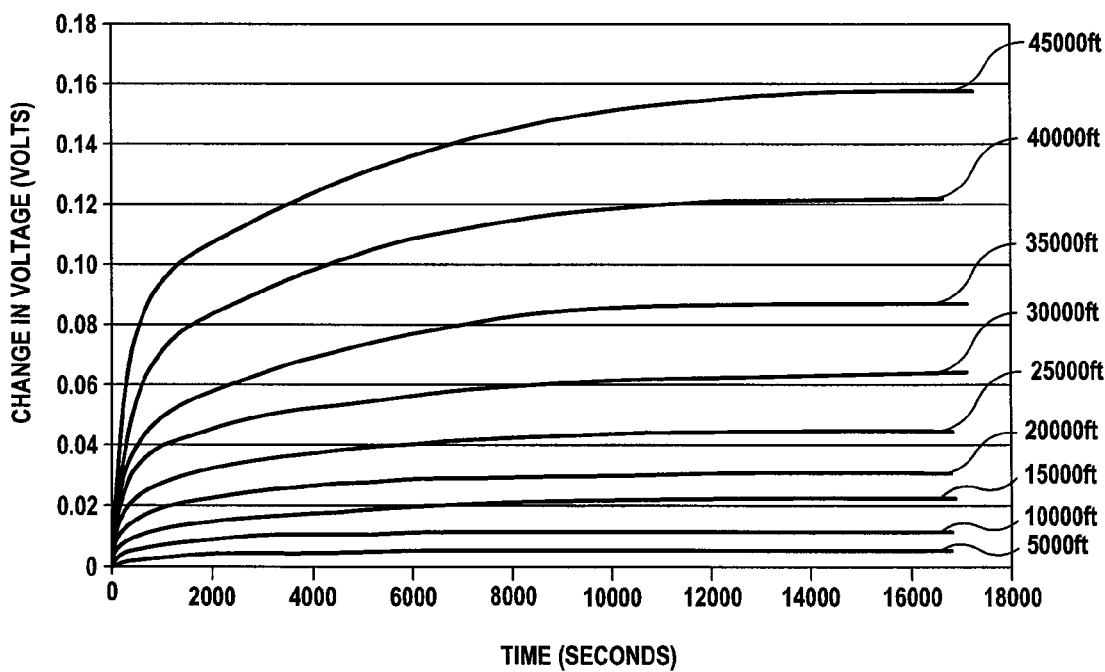
FIG. 3 is a plot of change in photodiode voltage with time, at 1100 rpm agitation, for simulated altitudes of 5000 ft to 45000 ft.

The rate of oxygen degassing was high upon initial exposure to the reduced pressure then decreased with time. To normalise the data and give an effective zero baseline and ΔV value, the first 30 data points, before exposure to the simulated altitude, were averaged and subtracted from voltage values recorded. This process was repeated for simulated altitude values of 40000 to 5000 feet at 5000 feet intervals and the ΔV calculated for each. As can be seen in FIG. 3, when the effective altitude is lowered ΔV is reduced, denoting a drop in the total amount of oxygen degassed over an equal time period as expected.

To allow for the conversion of ΔV values to ppm $O_2$ values, the expected ppm $O_2$ at given altitudes were calculated using an analytical method specifically created for this purpose. The technique was implemented following the approach detailed in ASTM International Designation D2779-92 (2002) "Standard Test Method for Estimation of Solubility of Gases in Petroleum Liquids" (available from ASTM International, 100 Barr Harbor Drive, PO Box C700, West Conshohocken, Pa., 19428-2959 USA). The change in voltage associated with a simulated altitude and its calculated ppm $O_2$ value are shown in Table 1.

TABLE 1

Table of data for the calculation of ppm $O_2$ from experimental $\Delta V$ values

| Altitude (feet) | Calculated ppm $O_2$ (ASTM) | $\Delta V$ for altitude (volts) |
|---|---|---|
| 0 | 83 | 0 |
| 5000 | 69.1 | 0.008316 |
| 10000 | 57 | 0.01836 |
| 15000 | 46.8 | 0.031158 |
| 20000 | 38.2 | 0.045226 |
| 25000 | 30.8 | 0.064069 |
| 30000 | 24.7 | 0.082199 |
| 35000 | 19.6 | 0.106628 |
| 40000 | 15.4 | 0.137392 |
| 45000 | 12.1 | 0.168189 |

Figure 4:
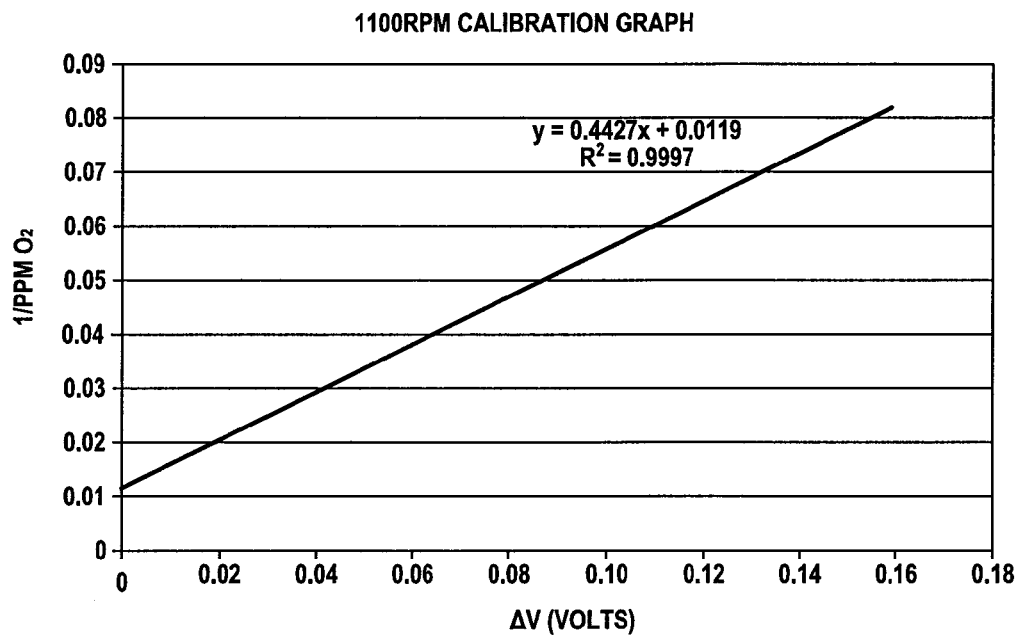
FIG. 4 is a calibration graph for the 1100 rpm agitation data set, showing the reciprocal of $O_2$ concentration as a function of photosensor voltage.

The change in voltage for each simulated altitude was then plotted against the calculated ppm $O_2$ to give a calibration curve (FIG. 4). A linear correlation between the reciprocal of ppm $O_2$ and $\Delta V$ was found (as shown in FIG. 4), thereby allowing for the conversion of $\Delta V$ to ppm $O_2$.

Figure 5:
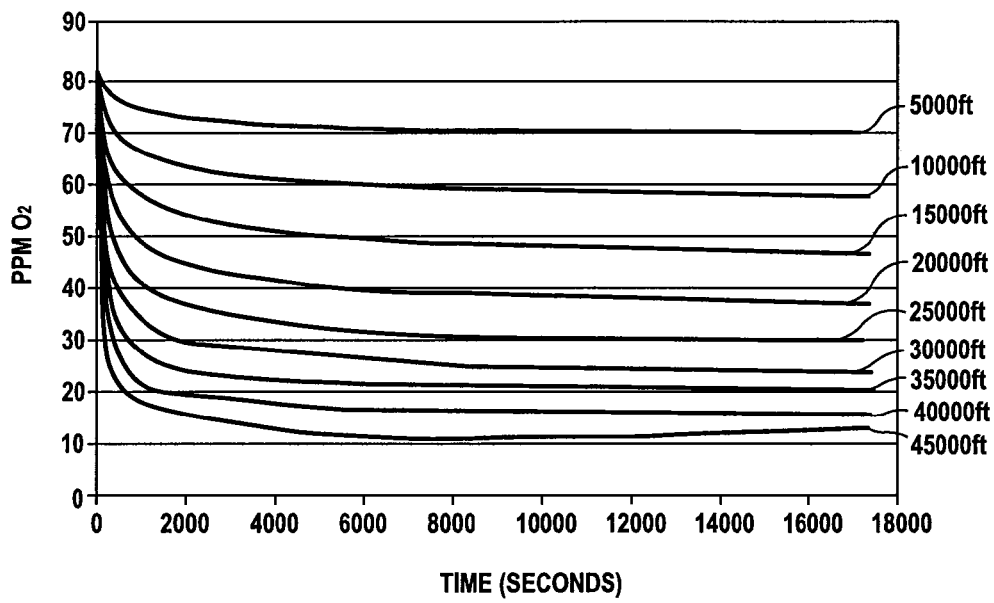
FIG. 5 is an oxygen degassing profile for all simulated altitudes at 1100 rpm agitation.

The calibration equation generated allowed the conversion of the $\Delta V$ values to ppm $O_2$ values and a graph charting oxygen degassing over time to be plotted (FIG. 5).

Figure 6:
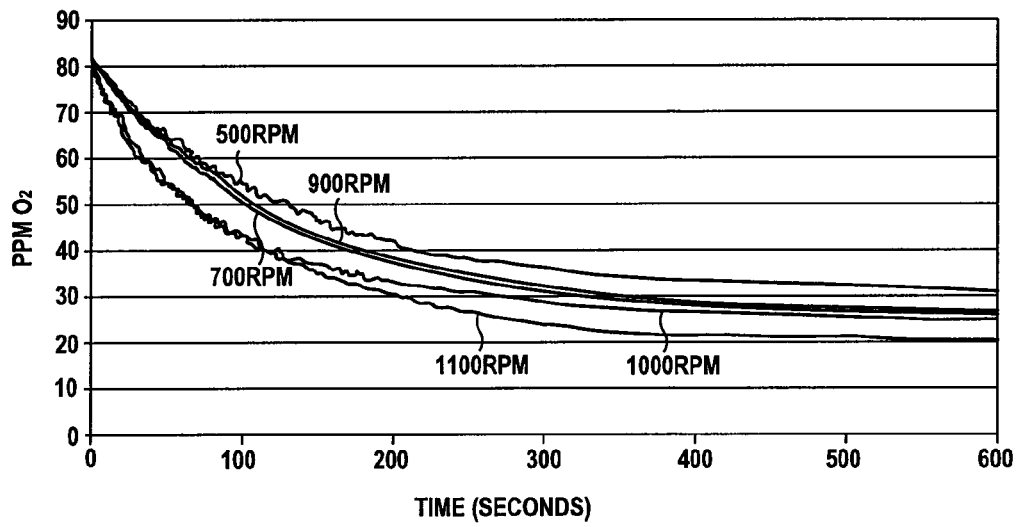
FIG. 6 is a plot giving a comparison of degassing profiles from 80 ppm for all agitation rates at a simulated altitude of 45000 feet.

The same process was applied to all agitation rates. To test the robustness of the method, the calibration curves generated for each of the agitation rates were compared. The normalised data were then plotted and the calibration curves for each agitation rate compared. FIG. 6 shows a direct comparison of oxygen degassing for all agitation rates from 80 ppm oxygen.

To test the effect of temperature on the rate of degas at a given agitation rate, two experiments were compared. The test apparatus was set at a simulated altitude of 35000 feet, an agitation rate of 1100 rpm and a temperature of 20° C. Data were collected in the usual manner outlined above. On completion the Porphyrin-A solution was changed and the apparatus left to equilibrate at 20° C. Once equilibrated the temperature of the circulating water was set to 5° C. and the voltage logged. Once equilibrated at 5° C. the data logging software was reset and the experiment conducted as for 20° C.

Figure 7:
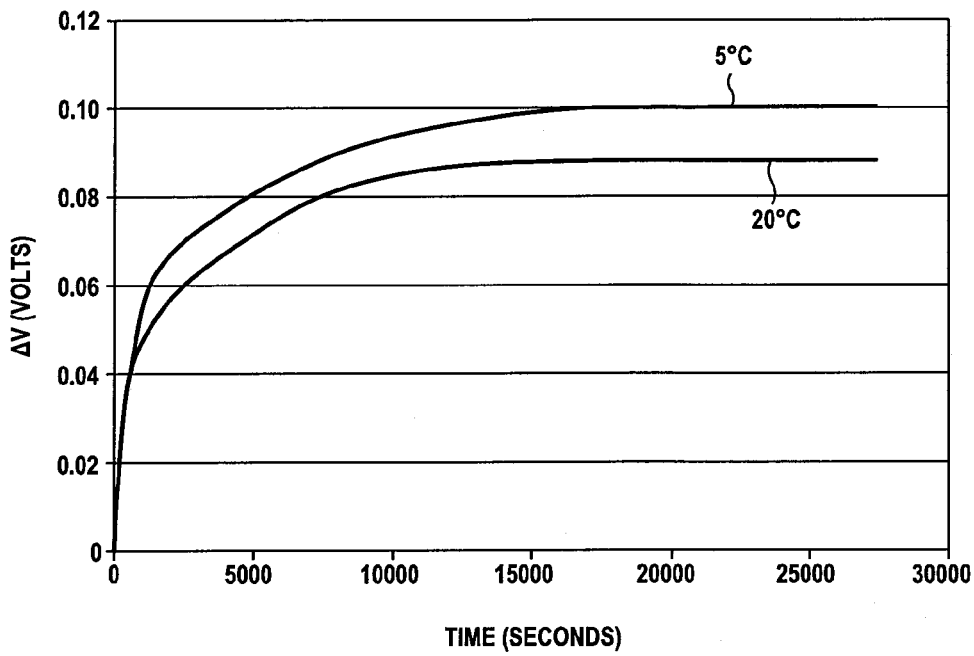
FIG. 7 is a plot showing a comparison of 20° C. and 5° C. degassing rates at 1100 rpm agitation and 35000 feet.

The output voltage after equilibration at $T_0$ and 20° C. was 0.141 V. On changing the temperature of the circulating water to 5° C. the voltage output was seen to increase indicating an increase in phosphorescence at the lower temperature. A comparison of the 20° C. and 5° C. temperature runs can be seen in FIG. 7.

Figure 8:
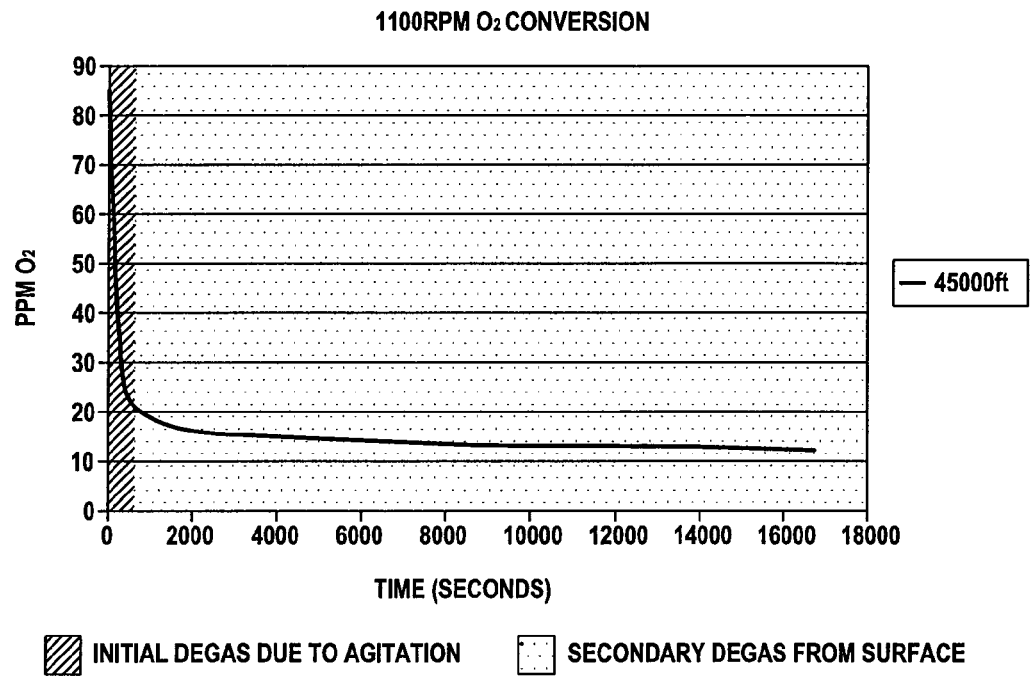
FIG. 8 is a plot of the 45000 feet 1100 rpm agitation oxygen degassing profile, showing two modes of degassing.
Figure 9:
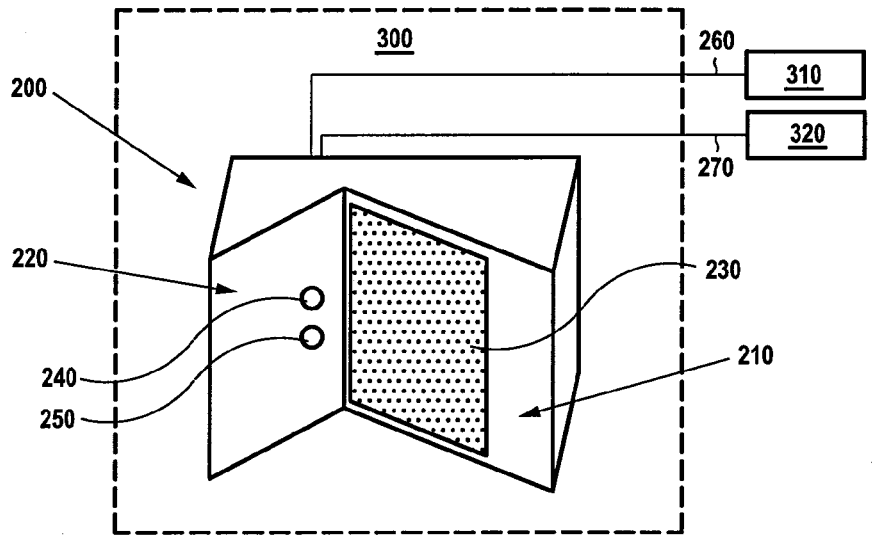
FIG. 9 is a perspective view of a sensor according to one embodiment of the invention.

Overall, it was noted that the amount of oxygen degassed at a given agitation rate showed the expected drop when the effective simulated altitude is increased. Degas curves when converted to parts per million oxygen show a distinct two stage curve (FIG. 8). It is speculated that this distinctive two stage curve may be as a result of different modes of degassing.

The initial large gradient observed may be due to the degassing of oxygen via the formation of bubbles generated by the agitation of the solution by the magnetic follower. The darker shaded portion of FIG. 8 highlights the first 10 minutes of the degas profile and accounts for approximately 85% of the total degas.

Without being bound by any particular theory, it is thought that the second mode of degas, from 10 minutes onwards, is due to surface degassing (the lighter shaded portion of FIG. 8).

This same general pattern is seen for all agitation rates and simulated altitudes.

A comparison of the degas rates at 45000 feet for agitation speeds of 1100, 1000, 900, 700 and 500 rpm, showed that, as expected, the higher the agitation rate the faster the initial degassing rate. Expansion of the first 10 minutes of the degas curves for the 45000 feet results and rate of degas from 80 ppm $O_2$ (FIG. 6) allow a closer comparison of initial degas rates. The initial rate of degas, up to 150 seconds, for the 1100 and 1000 rpm agitation curves are very comparable. After 150 seconds the 1000 rpm result drops away and after 600 seconds is only marginally higher than the 900 and 700 rpm results.

The 900 and 700 rpm results show a high degree of continuity over the first 1000 seconds. Following 1000 seconds, the 700 rpm curve drops away and the 900 rpm curve follows closer to the 1000 rpm.

If the shape of the degas curve is in fact due to the two modes of degassing, as described earlier, it would imply that initial degas rates increase with agitation rate. Secondary degas, from the surface of the kerosene, may have an optimum rate in the 900 to 1000 rpm range.

Before assessing the effect of temperature on the rate of degassing of a solution of Porphyrin-A kerosene, it was necessary to assess the effect of temperature on the phosphorescence properties of the Pt porphyrin complex. To this end a standard solution was equilibrated at 20° C. as described above. Once a steady state was established the data logging software was reset and the thermostat on the water bath set to 5° C. There was an increase in voltage due to an increase in phosphorescence following a change in temperature. The overall increase in voltage from 20 to 5° C. was recorded as 0.014 volts.

A comparison of the degas profiles (FIG. 7) shows that the initial rates of degassing for both temperatures are equivalent.

The calculated difference in oxygen content, using the ASTM spread supplied, from 5 to 20° C. is less than 1 ppm. It was therefore concluded that the higher final voltage recorded was due to the increase in phosphorescence of the Pt porphyrin complex at the reduced temperature.

The skilled person will appreciate that further experiments at lower temperatures may show a greater increase in phosphorescence. This would lead to a higher response from the photodiode and the possibility of decreasing the concentration of the Pt porphyrin complex to achieve the same overall change in voltage across a degas profile. Further reductions in temperature will necessitate the experimental apparatus being in a controlled environment to control the formation of condensation on electrical components.

The reproducibility of the experimental method was tested twice. The 1000 rpm agitation, 45000 feet experiments were conducted with 8 degas experiments in between, the 900 rpm 35000 feet with 15. Both results show a good degree of reproducibility.

Data sets were originally processed as they were generated. Conversion of $\Delta V$ to ppm $O_2$ values for all agitation rates were via the generation of calibration graphs. Initial results for 1000 rpm agitation showed that the relationship between $\Delta V$ and ppm $O_2$ was not linear. The calibration graphs generated were based on fourth-order polynomial curves fitted to the raw data.

Once all the data had been collected and the calibration curves compared it was clear that the 1100 rpm agitation rate did not follow the same pattern as the other agitation rates. Further investigation of the relationship between ppm $O_2$ and the recorded $\Delta V$ value showed that 1/ppm $O_2$ plotted against $\Delta V$ gave a straight line for the 1100 rpm agitation rate.

When this calibration method was applied to data from other agitation rates the linearity of the result was reduced.

It is concluded that oxygen concentrations at very low levels down to 10 parts per million (and very likely further, if required) are readily detectable in kerosene by monitoring the degree of phosphorescence of Pt(II) meso-tetra(pentafluorophenyl) porphyrin in solution. The measurement of the phosphorescence was successfully used to observe degassing of kerosene at different pressures and at different stirring rates. A well-defined pattern of oxygen release was observed at high stirring rates. Typically 85% of the total degassing occurred in the first 10 minutes. At low stirring rates anomalous effects occurred. Preliminary experiments show that the platinum porphyrin complex will operate at low temperatures in kerosene for oxygen concentration detection.

In the initial experiments, the porphyrin was coated onto a substrate and in the later experiments it was dissolved in the fuel itself. Using a coated substrate has the advantage that the dye is localised and can be replaced easily. Dissolving the dye in the fuel has the advantage that the light source and sensor can be placed anywhere in the fuel tank and piping. Alternative variants are envisaged including coating the dye onto transparent walls of tubing through which the fuel is piped. In a variation of that approach, optical fibres could be arranged adjacent to the tube, the fibres being used to transmit UV to, and detect phosphorescence at, fixed points along the tube. That approach would also readily permit other characteristics of the phosphorescence to be measured, if desired, such as time constants of phosphorescence with UV pulsing. The use of multiple point source measurements by the use of optical fibres is likely to be the lowest risk strategy in terms of cost control. A further advantage is that non-invasive measurements can be undertaken with the use of a transparent window in a tank or piping.

It is also envisaged in yet a further embodiment that the dye may be anchored to a gel, for example a silica gel, in order to stop or reduce leaching of the porphyrin.

According to this variant, the porphyrin silica gel is then immobilised within a polymer matrix. The porphyrin silica gel is then added to dichloromethane (DCM) or other suitable solvent and the resulting solution applied to a surface of Perspex. The DCM or similar dissolves the surface layer of the Perspex, and on evaporation leaves the silica gel particles immobilised on the Perspex surface. This embodiment yields an active layer that shows good phosphorescence in absence of oxygen and with good resistance to the leaching effects of the kerosene.

In a further exemplary embodiment of the invention, sensor 200 is mounted on a wall 300 of an aircraft fuel tank. In alternative embodiments, the sensor may be mounted on any suitable structure within the tank. Sensor 200 is a block-shaped, with a region removed having the shape of a prism, providing two adjacent surfaces 210, 220. The two surfaces 210, 220 join each other at approximately a right angle.

On surface 210, there is mounted a Perspex sheet impregnated with porphyrin-silica gel, as described above. On surface 220, close its junction with surface 210, are two holes 240, 250, each of which contains an optical fibre 260, 270. The fibre 260 in hole 240 runs back through block 200, out of the fuel tank, to a UV LED 310. In the front of the end of the fibre 270 in hole 250 is a red filter for passing light at a wavelength at 608 nm. The fibre 270 runs back through block 200, out of the fuel tank, to a photodiode 320.

In use, UV light (with intensity peaking at a wavelength of 400 nm) from LED 310 passes along the fibre 260 in hole 240 and irradiates sheet 230, causing phosphorescence. Some of the phosphorescence passes via the red filter, is captured by the fibre 270 in hole 250, and channelled back to the photodiode 320.

As the oxygen concentration in the fuel tank changes, so the amount of phosphorescence detected by photodiode 320 changes, as discussed above. Calibration of the output from photodiode 320 allows the concentration of oxygen in the fuel tank to be monitored in real time. This latter aspect may be particularly important for in-service dissolved oxygen measurements such as during flight and in other mission modes.

According to this embodiment, sensor 200 is submerged in the aviation fuel and the concentration of oxygen in the fuel is measured directly. In yet an alternative embodiment, sensor 200 is positioned in the ullage above the fuel, and the concentration of oxygen in the ullage is measured. The temperature of the fuel may be measured and its effect on the operation of the sensor compensated for.

Whilst the present invention has been described and illustrated with reference to particular embodiments, it will be appreciated by those of ordinary skill in the art that the invention lends itself to many different variations not specifically illustrated herein. Some examples of such variations and alternatives have been described above. Furthermore, a different and suitable compound may exist which exhibits optical sensitivity to gases other than oxygen. Such compounds may be used to form a monitor for measuring the concentration of such other gases in or adjacent to aviation fuel using optical techniques similar to those described herein. The sensor of the above-described example embodiment may be used in a gas concentration monitor for monitoring the concentration of a gas different from that directly sensed by the sensor, by means of inference in cases where the concentration of different gases are inter-related. The fuel tank in which the sensor is mounted may be in an aircraft or may be in a fuel tanker for refueling aircraft. The sensor may also have application in other area of the aircraft industry, possibly, but not necessarily, in relation to monitoring gas levels in or next to aircraft fuel. For example, the sensor could be used on a fuel tanker for delivering fuel to an aircraft. With appropriate modification, the sensor could also be used to monitor the oxygen level in the cabin for passengers comfort. Another related application could relate to monitoring the oxygen level in the cargo hold for live animal comfort. In either case, the oxygen levels could be periodically monitored to ensure that the levels meet certain criteria, such as staying within an acceptable range deemed to provide a comfortable and pleasant environment. If the oxygen levels do not meet the criteria set, then remedial action could be taken, for example either by diluting oxygen levels by means of introducing Nitrogen or NEA (if the detected oxygen concentration is too high), or by introducing Oxygen, or Oxygen enriched air (if the detected oxygen concentration is too low). Different filters may be associated with the light source (e.g. the LED) and/or the light detector (e.g. the photodiode). The sensor may be able to function adequately without any filters.

The exemplary experiments described above show that photodiode voltage shift, measuring phosphorescence intensity, as a function of time, may provide data from which correlation with dissolved $O_2$ levels in the kerosene samples can be calculated. Using such a method $O_2$ degas profiles of the kerosene samples over a range of pressure altitudes and agitation levels may be obtained. The applicants have found that the effects of reducing atmospheric pressure and increasing agitation yield a significant increase in $O_2$ evolution rate. The applicants have shown the degas profiles to be non-linear and exhibited asymptotic behaviour over time. The degas profile may be represented with a first order exponential decay model yielding satisfactory correlation coefficients. It will be appreciated that further mathematical models may be developed by repeating the experimental example above to verify the effects on O2 evolution rate of varying the temperature of the kerosene. Where in the foregoing description, integers or elements are mentioned which have known, obvious or foreseeable equivalents, then such equivalents are herein incorporated as if individually set forth. Reference should be made to the claims for determining the true scope of the present invention, which should be construed so as to encompass any such equivalents. It will also be appreciated by the reader that integers or features of the invention that are described as preferable, advantageous, convenient or the like are optional and do not limit the scope of the invention. Moreover, it is to be understood that such optional integers or features, whilst of possible benefit in some embodiments of the invention, may not be desirable, and may therefore be absent, in other embodiments.

The invention claimed is:

1. A fuel tank gas monitor for monitoring the concentration of a gas in a fluid comprising aviation fuel, the monitor comprising:
   a gel;
   a substance anchored to the gel in such a way as to at least reduce leaching of the substance into the fluid, the optical properties of the substance changing when the substance is exposed to the gas;
   a light source, arranged to irradiate the substance with light; and
   a photosensor, arranged to detect light from the substance.

2. A monitor as claimed in claim 1, wherein the substance is carried by a solid substrate.

3. A monitor as claimed in claim 1, wherein the monitor is arranged for monitoring the concentration of the gas dissolved in liquid aviation fuel.

4. A monitor as claimed in claim 1, wherein the monitor is arranged for monitoring the concentration of the gas in an ullage space.

5. A monitor as claimed in claim 1, wherein the monitor is associated with a signal processing unit arranged to generate and output a signal derived from a measurement of intensity of light detected by the photosensor at a time when the substance is being irradiated by the light source.

6. A monitor as claimed in claim 1, wherein the gas is oxygen.

7. A monitor as claimed in claim 1, wherein the substance is a photochromic substance.

8. A monitor as claimed in claim 1, wherein the substance is a chromophore-metal complex.

9. A monitor as claimed in claim 1, wherein the substance is a porphyrin.

10. A monitor as claimed in claim 1, wherein the change of the optical properties of the substance is a change in absorption of the light from the light source.

11. A monitor as claimed in claim 1, wherein the substance exhibits photoluminescence induced by the light from the light source, and the change of the optical properties of the substance is a change in the photoluminescence.

12. A monitor as claimed in claim 1, wherein the light source is arranged to irradiate the substance with ultraviolet (UV) light.

13. A monitor as claimed in claim 1, wherein the light source is a non-coherent light source.

14. A monitor as claimed in claim 1, wherein the light source has a power rating of less than 100 mW and is arranged to emit light having a maximum radiant intensity of less than 50 mW/Sr.

15. A monitor as claimed in claim 1, wherein the light source comprises one or more LEDs.

16. A monitor as claimed in claim 1, wherein the photosensor is arranged to detect light in visible spectrum.

17. A monitor as claimed in claim 1, wherein the monitor comprises a filter arranged between the photosensor and the substance.

18. A fuel tank including a monitor according to claim 1.

19. A vehicle including a fuel tank according to claim 18.

20. A passenger aircraft including a fuel tank according to claim 18.

21. A method of controlling an environment which comprises a fluid, wherein the method includes measuring the concentration of the gas in the environment by using a monitor according to claim 1.

22. A method according to claim 21, further comprising the step of introducing another gas different from the measured gas into the environment comprising the fluid, in dependence on the gas concentration of the measured gas, so as to dilute the concentration of the measured gas.

23. A method according to claim 21, further comprising the step of introducing more of the gas into the environment comprising the fluid, in dependence on the gas concentration of the measured gas, so as to increase the concentration of the measured gas.

24. A method according to claim 21, wherein aviation fuel is stored in the environment, whereby the fluid comprises aviation fuel.

25. A method according to claim 24, further comprising the step of degassing the fuel, in dependence on the gas concentration of the measured gas.

26. A fuel tank monitor for monitoring the concentration of a gas in a fluid, the monitor comprising:
   a gel;
   a substance anchored to the gel in such a way as to at least reduce leaching of the substance into the fluid and carried by a solid substrate, the optical properties of the substance changing when the substance is exposed to the gas;
   a light source, arranged to irradiate the substance with light; and
   a photosensor, arranged to detect light from the substance.

27. A method of monitoring the concentration of a gas in a fluid, the method comprising the steps of:
   a) providing, in a vessel containing the fluid, a substance carried by a solid substrate and anchored to a gel in such a way as to at least reduce leaching of the substance into the fluid, the optical properties of the substance changing when the substance is exposed to the gas;
   b) exposing the substance to light;
   c) detecting light from the substance; and
   d) monitoring changes in the detected light to determine changes in the concentration of the gas in the region of the substance.

28. A method as claimed in claim 27, wherein the fluid comprises aviation fuel.

29. A method as claimed in claim 28, wherein the concentration of the gas in aviation fuel is monitored directly, with the substance immersed in the fuel.

30. A method as claimed in claim 28, wherein the concentration of the gas in the aviation fuel is monitored indirectly, with the aviation fuel contained in a container having an ullage space above the fuel and the substance being positioned in the ullage space of the container.

31. A method of monitoring, in a passenger aircraft, the concentration of a gas in a fluid comprising aviation fuel, the method comprising:

a) providing, in a fuel tank containing the aviation fuel, a substance anchored to a gel in such a way as to at least reduce leaching of the substance into the fluid, the optical properties of the substance changing when the substance is exposed to the gas;
b) exposing the substance to light;
c) detecting light from the substance; and
d) monitoring changes in the detected light to determine changes in the concentration of the gas in the region of the substance.

32. A method as claimed in claim 31, wherein the concentration of the gas in aviation fuel is monitored directly, with the substance immersed in the fuel.

33. A method as claimed in claim 31, wherein the concentration of the gas in the aviation fuel is monitored indirectly, with the aviation fuel contained in a container having an ullage space above the fuel and the substance being positioned in the ullage space of the container.

* * * * *